United States Patent [19]

Takematsu et al.

[11] 4,284,813
[45] Aug. 18, 1981

[54] BENZAMIDE DERIVATIVES AND HERBICIDAL COMPOSITION CONTAINING THE SAME

[75] Inventors: Tetsuo Takematsu; Masaaki Hoya, both of Utsunomiya, Japan

[73] Assignee: Hodogaya Chemical Co., Ltd., Tokyo, Japan

[21] Appl. No.: 94,848

[22] Filed: Nov. 16, 1979

[30] Foreign Application Priority Data

Dec. 5, 1978 [JP] Japan .................. 53-149633

[51] Int. Cl.³ .................. C07C 103/22; C07C 103/28
[52] U.S. Cl. .................. 564/168; 564/170; 71/118
[58] Field of Search .................. 260/558 P, 558 A; 71/118; 564/168, 170

[56] References Cited

U.S. PATENT DOCUMENTS 3,340,042  9/1957  Schwartz .................. 71/118

OTHER PUBLICATIONS

Heller, "Arylamides of Aromatic Carboxylic, etc.", (1929), CA 23, p. 3909 (1929).
Yabutani et al., "Quinazolines", (1974), CA 82, No. 43453k, (1975).
Inove et al., "2-Aminobenzamide Ders.", (1973), CA 79, No. 136,857y, (1973).
Satzinger et al., "Antisecretory ... etc.", (1971), CA 76, No. 3908g, (1972).

*Primary Examiner*—Glennon H. Hollrah
*Attorney, Agent, or Firm*—Oblon, Fisher, Spivak, McClelland & Maier

[57] ABSTRACT

A herbicidal composition comprises a novel compound of benzamide derivative having the formula

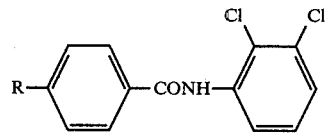

wherein R represents a straight or branched chain alkyl group; a straight or branched chain alkoxy group; or amino group.

1 Claim, No Drawings

BENZAMIDE DERIVATIVES AND HERBICIDAL COMPOSITION CONTAINING THE SAME

BACKGROUND OF THE INVENTION

1. Field of the Invention

The present invention relates to novel benzamide derivatives and herbicidal compositions containing the benzamide derivative.

2. Description of the Prior Arts

Recently, many herbicides have been proposed and practically used to contribute for elimination of agricultural labour works.

Thus, various problems on herbicidal effects and safety of the herbicides have been found in the practical applications.

It has been required to find improved herbicides which have no adverse effect to the object plants and effective to noxious weeds in a small dose of the active ingredient and significantly safe without any environmental pollution.

The inventors have synthesized various benzamides so as to find satisfactory herbicides and have studied herbicidal effects thereof, and the present invention has been attained.

SUMMARY OF THE INVENTION

It is an object of the present invention to provide specific benzamide derivatives and herbicidal compositions containing the same as an active ingredient.

The foregoing and other objects of the present invention have been attained by providing novel benzamide derivatives having the formula

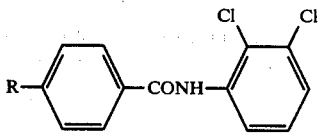

wherein R represents a straight or branched chain alkyl group, alkoxy group or amino group.

The herbicidal composition of the present invention comprises the novel benzamide derivative as an active ingredient and an adjuvant.

DETAILED DESCRIPTION OF THE PREFERRED EMBODIMENTS

The typical novel benzamide derivatives of the present invention include as follows.

| Compound | | Physical property |
|---|---|---|
| No. 1: | 4-methyl-N-(2,3-dichlorophenyl)-benzamide | m.p. 112–113° C. |
| No. 2: | 4-isopropyl-N-(2,3-dichlorophenyl)-benzamide | m.p. 102–104° C. |
| No. 3: | 4-n-propyl-N-(2,3-dichlorophenyl)-benzamide | m.p. 87.5–90° C. |
| No. 4: | 4-n-butyl-N-(2,3-dichlorophenyl)-benzamide | m.p. 64.5–66° C. |
| No. 5: | 4-t-butyl-N-(2,3-dichlorophenyl)-benzamide | m.p. 108.5–110.5° C. |
| No. 6: | 4-n-amyl-N-(2,3-dichlorophenyl)-benzamide | m.p. 66–68° C. |
| No. 7: | 4-n-hexyl-N-(2,3-dichlorophenyl)-benzamide | m.p. 57.5–61° C. |
| No. 8: | 4-n-octyl-N-(2,3-dichlorophenyl)-benzamide | m.p. 58.5–61° C. |
| No. 9: | 4-methoxy-N-(2,3-dichlorophenyl)-benzamide | m.p. 139–141° C. |
| No. 10: | 4-ethoxy-N-(2,3-dichlorophenyl)-benzamide | m.p. 140.5–142.5° C. |
| No. 11: | 4-n-propoxy-N-(2,3-dichlorophenyl)-benzamide | m.p. 115–116.5° C. |
| No. 12: | 4-n-butoxy-N-(2,3-dichlorophenyl)-benzamide | m.p. 108–109° C. |
| No. 13: | 4-n-hexyloxy-N-(2,3-dichlorophenyl)-benzamide | m.p. 99.5–101° C. |
| No. 14: | 4-n-octyloxy-N-(2,3-dichlorophenyl)-benzamide | m.p. 104–105.5° C. |
| No. 15: | 4-n-dodecyloxy-N-(2,3-dichlorophenyl)-benzamide | m.p. 95.5–97° C. |
| No. 16: | 4-amino-N-(2,3-dichlorophenyl)-benzamide | m.p. 202–203.5° C. |
| No. 17: | 4-n-pentoxy-N-(2,3-dichlorophenyl)-benzamide | m.p. 106–107° C. |
| No. 18: | 4-n-heptoxy-N-(2,3-dichlorophenyl)-benzamide | m.p. 91.5–93° C. |
| No. 19: | 4-n-heptyl-N-(2,3-dichlorophenyl)-benzamide | m.p. 68.5–70° C. |
| No. 20: | iso-butoxy-N-(2,3-dichlorophenyl)-benzamide | m.p. 119.5–120.4° C. |
| No. 21: | sec-butoxy-N-(2,3-dichlorophenyl)-benzamide | m.p. 104.5–105.5° C. |

The novel benzamide derivatives having the formula

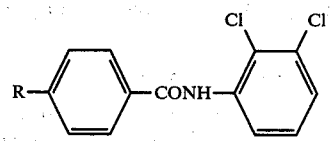

wherein R represents a straight or branched chain alkyl group, alkoxy group or amino group which have high purity can be easily obtained at high yield by reacting a specific benzoylchloride with 2,3-dichloroaniline in the presence of a basic salt such as potassium carbonate and sodium carbonate or an organic base such as pyridine and triethylamine, in an aqueous solution or an organic solvent such as acetone, benzene, toluene, tetrahydrofuran and dioxane.

Typical examples for preparations of the compounds will be illustrated.

PREPARATION 1

A mixture of 1.0 g. of p-methyl benzoic acid, 3.0 g. of thionyl chloride, 5 ml. of toluene and a small amount of zeolite was refluxed for about three hours to react them. After the reaction, excess of thionyl chloride, dissolved hydrogen-chloride gas, sulfur dioxide gas and toluene were vaporized to remove them by a rotary evaporator. A crude p-methyl benzoylchloride was obtained as a residue. On the other hand, 1.2 g. of 2,3-dichloroaniline and 1.0 g. of triethylamine were dissolved in 10 ml. of acetone and the resulting solution of the crude p-methyl benzoylchloride in 5 ml. of acetone was added dropwise with stirring at room temperature for about 5 minutes. After the addition, the mixture is stirred at room temperature for 5 hours to complete the reaction. After the reaction, the reaction mixture was poured into about 200 ml. of 2–3% aqueous solution of hydrochloric acid whereby fibrous precipitate was obtained. The precipitate was separated by a filtration and the residue was washed with a dilute alkaline solution and then, with water and dried in air, and recrystallized from toluene to obtain 1.5 g. of 4-methyl-N-(2,3-dichlorophenyl)benzamide as the object product. The yield was 72.9% and the melting point was 112°–113° C.

PREPARATION 2

A mixture of 1.1 g. of p-n-butyl benzoic acid, 2.5 g. of thionylchloride, 5 ml. of toluene and a small amount of zeolite was refluxed for about 4 hours to react them. After the reaction, excess of thionylchloride, dissolved hydrogen-chloride gas, sulfur dioxide gas, and toluene were vaporized to remove them by a rotary evaporator. A crude p-n-butyl benzoylchloride was obtained as a residue. On the other hand, 1.1 g. of 2,3-dichloroaniline was dissolved in 10 ml. of acetone and 1.3 g. of potassium carbonate was gradually added with stirring to suspend it.

In the suspension, the solution of the crude p-n-butyl benzoylchloride in 10 ml. of acetone was added dropwise during about 5 minutes with stirring at room temperature. After the addition, the stirring was continued at room temperature for 7 hours to complete the reaction. After the reaction, the reaction mixture was poured into about 200 ml. of 5% hydrochloric acid whereby fibrous precipitate was obtained. The precipitate was separated by a filtration and the residue was washed with a dilute alkaline solution and then, with water and dried in air to obtain 1.5 g. of 4-n-butyl-N-(2,3-dichlorophenyl)benzamide as the object product. The yield was 75.4% and the melting point was 64.5°–66.0° C.

PREPARATION 3

A mixture of 1.2 g. of p-n-octyloxybenzoic acid, 3.0 g. of thionychloride, 5 ml. of toluene and a small amount of zeolite was refluxed for about 4 hours to react them.

After the reaction, excess of thionylchloride, dissolved hydrogenchloride gas, sulfur dioxide gas and toluene were vaporized to remove them by a rotary evaporator. A crude p-n-octyloxybenzoylchloride was obtained as a residue.

On the other hand, 0.85 g. of 2,3-dichloroaniline and 0.6 g. of triethylamine were dissolved in 3 ml. of tetrahydrofuran. A solution of the resulting crude p-n-octyloxybenzoylchloride in 5 ml. of tetrahydrofuran was added dropwise at room temperature for about 5 minutes with stirring. After the addition, the mixture was stirred at room temperature for about 1 day to complete the reaction. After the reaction, the reaction mixture was poured into about 300 ml. of 2% aqueous solution of hydrochloric acid to obtain fibrous precipitate. The precipitate was separated by a filtration and the residue was washed with a diluted alkaline solution and then, with water and dried and recrystallized from toluene to obtain 4-n-octyloxy-N-(2,3-dichlorophenyl)-benzamide. The yield was 66.1%. The melting point was 104°–105.5° C.

The herbicidal compositions of the present invention can be obtained by admixing the active ingredient with a desired adjuvant so as to form a wettable powder, an emulsifiable concentrate, a dust, a granule etc..

The liquid adjuvant is usually an organic solvent and the solid adjuvant is usually mineral fine powder. In order to impart emulsifiable property, dispersable property and spreadable property, a desired surface active ingredient is added. The active ingredient can be used by admixing with an agricultural chemical such as a fertilizer, a herbicide, an insecticide and a germicide.

The active ingredient of the compound of the present invention is applied depending upon a weather condition, a soil condition, a form of the composition, a season of the application and a method of the application and kinds of crop plants and kinds of weeds. The active ingredient is usually applied in a range of 0.01 to 10 kg preferably 0.1 to 5 kg especially 0.5 to 3 kg per 1 hectare in the treatment and it is usually applied in a concentration of 10 to 10,000 ppm preferably 100 to 5,000 ppm especially 250 to 3,000 ppm of the active ingredient. Suitable adjuvants include solid carrier such as jeeklite, talc, bentonite, clay, kaolin, diatomaceous earth, silica gel, vermiculite, lime, and liquid carriers such as toluene, xylene, isophorone, dioxane, acetone, cyclohexanone, methyl naphthalene alcohols or dimethylformamide; and surfactants as emulsifiers dispersing agents or wetting agents such as alkylsulfonate, alkylbenzenesulfonate, alkyl sulfate, polyoxyethyleneglycol ethers, polyoxyethylenealkylaryl ethers or polyoxyethylenesorbitan monoalkylate.

The amounts of the active ingredients, adjuvants and additives in the herbicidal compositions of the present invention will be further illustrated.

Emulsifiable concentrate

Active ingredient:2 to 80 wt.% preferably 5 to 40 wt.%;

Surfactant: 1 to 40 wt.% preferably 5 to 20 wt.%;

Liquid carrier: 5 to 95 wt.% preferably 50 to 90 wt.%.

Wettable powder

Active ingredient: 1 to 50 wt.% preferably 5 to 30 wt.%;

Surfactant: 0.5 to 20 wt.% preferably 1 to 10 wt.%;

Solid carrier: 5 to 99 wt.% preferably 50 to 95 wt.%.

Dust

Active ingredient: 0.5 to 10 wt.% preferably 1 to 5 wt.%;

Solid carrier: 90 wt.% 99.5 wt.% preferably 95 to 99 wt.%.

The herbicidal compositions of the present invention mainly suppress seadling and growth of weeds. The herbicidal compositions impart excellent herbicidal effect for gramineous weeds of barnyard grass, marsh grass, sprangletop by a soil treatment in a flooded condition. No phytotoxicity to transplanted rice seedling is not found. Thus, the herbicidal composition has high selectivity.

The herbicidal compositions of the present invention will be illustrated by certain examples.

EXAMPLE 1 (Wettable Powder)

| | |
|---|---|
| Jeeklite | 97 wt. parts |
| Neopelex powder(Kao-Atlas Co.) | 1.5 wt. parts |
| Sorpol 800 A(Toho Kagaku Kogyo) | 1.5 wt. parts |

These components were uniformly pulverized and mixed to prepare a carrier for wettable powder.

The resulting carrier for wettable powder (90 wt. parts) and 4-methyl-N-(2,3-dichlorophenyl)-benzamide (10 wt. parts) were uniformly pulverized and mixed to obtain a wettable powder.

EXAMPLE 2 (Emulsifiable concentrate)

| | |
|---|---|
| 4-Methyl-N-(2,3-dichlorophenyl)-benzamide | 10 wt. parts |
| Cyclohexanone | 30 wt. parts |
| Xylene | 50 wt. parts |
| Sorpol 800 A(Toho Kagaku Kogyo) | 10 wt. parts |

The components were uniformly mixed to obtain an emulsifiable concentrate.

Test 1

Each porcelain pot of 1/15,500 are was filled with paddy soil and seeds of barnyard grass, marsh grass, sprangletop were uniformly sown on the surface layer, and flooded in a depth of 2 cm. Two seedlings of rice (species: Nihon bare) at two leaf stage were transplanted. At the time of germination of the weeds, each diluted solution of a wettable powder containing each active ingredient was poured into water at each dose of the active ingredient. Twenty days after the treatment with the active ingredient, the herbicidal effect to barnyard grass, marsh grass, sprangletop and the phytotoxicity to the transplanted rice seedlings were observed. The test results are shown by the following ratings.

| Herbicidal effect | Phytotoxicity to transplanted rice seedling |
|---|---|
| 0: none | —: none phytotoxicity |
| 1: growth suppression of 20–30% | ±: substantial none-phytotoxicity |
| 2: growth suppression of 40–50% | +: slight damage |
| 3: growth suppression of 60–70% | ++: damage |
| 4: growth suppression of 80–90% | +++: remarkable damage |
| 5: complete growth suppression | |

The test results are shown in Table:

TABLE

| Compound No. | Dose g./10 are | Phytotoxicity of rice seedling | Herbicidal effect Barnyard grass | Marsh grass | Sprangletop |
|---|---|---|---|---|---|
| 1 | 1000 | ± | 5 | 5 | 5 |
| | 500 | — | 5 | 5 | 5 |
| | 250 | — | 5 | 5 | 5 |
| | 125 | — | 4.5–5 | 5 | 5 |
| 2 | 1000 | ± | 5 | 5 | 5 |
| | 500 | — | 5 | 5 | 5 |
| | 250 | — | 5 | 5 | 5 |
| | 125 | — | 5 | 5 | 5 |
| 4 | 1000 | ± | 5 | 5 | 5 |
| | 500 | — | 5 | 5 | 5 |
| | 250 | — | 5 | 5 | 5 |
| | 125 | — | 5 | 4.5 | 4.5 |
| | 1000 | — | 5 | 5 | 5 |
| | 500 | — | 5 | 5 | 5 |
| 6 | 250 | — | 5 | 5 | 5 |
| | 125 | — | 4.5–5 | 4.5–5 | 4.5 |
| | 1000 | — | 5 | 5 | 5 |
| | 500 | — | 5 | 5 | 5 |
| 7 | 250 | — | 5 | 5 | 5 |
| | 125 | — | 4.5 | 4.5 | 4.5 |
| | 1000 | — | 5 | 5 | 5 |
| | 500 | — | 5 | 5 | 5 |
| 11 | 250 | — | 5 | 5 | 5 |
| | 125 | — | 4.5–5 | 4.5 | 4.5 |
| | 1000 | ± | 5 | 5 | 5 |
| | 500 | — | 5 | 5 | 5 |
| 12 | 250 | — | 5 | 5 | 5 |
| | 125 | — | 5 | 5 | 5 |
| | 1000 | — | 5 | 5 | 5 |
| | 500 | — | 5 | 5 | 5 |
| 13 | 250 | — | 5 | 5 | 5 |
| | 125 | — | 5 | 5 | 4.5 |
| | 1000 | — | 5 | 5 | 5 |
| | 500 | — | 5 | 5 | 5 |
| 16 | 250 | — | 5 | 5 | 5 |
| | 125 | — | 5 | 5 | 4.5 |
| | 1000 | — | 5 | 5 | 5 |
| | 500 | — | 5 | 5 | 5 |
| 17 | 250 | — | 4.5 | 4.5 | 4.5 |
| | 125 | — | 4–4.5 | 4 | 4–4.5 |
| | 1000 | — | 5 | 5 | 55 |
| | 500 | — | 4.5 | 4.5 | 4.5 |
| 20 | 250 | — | 4–4.5 | 4–4.5 | 4.5 |
| | 125 | — | 4 | 4 | 4–4.5 |
| | 1000 | ± | 5 | 5 | 5 |
| | 500 | — | 5 | 5 | 5 |
| 21 | 250 | — | 4.5–5 | 4.5–5 | 5 |
| | 125 | — | 4.5–5 | 4.5 | 4.5 |

We claim:
1. Benzamide derivatives having the formula

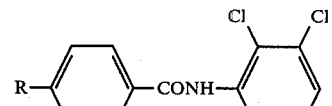

wherein R represents a straight or branched chain alkyl group, having 1 to 8 carbon atoms, a straight or branched chain alkoxy group having 1 to 12 carbon atoms; or an amino group.

* * * * *